(12) United States Patent
Chui et al.

(10) Patent No.: US 11,455,754 B2
(45) Date of Patent: Sep. 27, 2022

(54) SYSTEM AND METHOD FOR SYNTHESIZING LOW-DIMENSIONAL IMAGE DATA FROM HIGH-DIMENSIONAL IMAGE DATA USING AN OBJECT GRID ENHANCEMENT

(71) Applicant: HOLOGIC, INC., Marlborough, MA (US)

(72) Inventors: Haili Chui, Fremont, CA (US); Xiaomin Liu, Sunnyvale, CA (US); Xiangwei Zhang, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/497,766

(22) PCT Filed: Mar. 28, 2018

(86) PCT No.: PCT/US2018/024912
§ 371 (c)(1),
(2) Date: Sep. 25, 2019

(87) PCT Pub. No.: WO2018/183549
PCT Pub. Date: Oct. 4, 2018

(65) Prior Publication Data
US 2021/0118199 A1  Apr. 22, 2021

Related U.S. Application Data

(60) Provisional application No. 62/479,008, filed on Mar. 30, 2017.

(51) Int. Cl.
*G06T 11/00* (2006.01)
*G06N 20/00* (2019.01)
(Continued)

(52) U.S. Cl.
CPC ............ *G06T 11/005* (2013.01); *A61B 6/502* (2013.01); *G06N 20/00* (2019.01); *G06T 7/0012* (2013.01);
(Continued)

(58) Field of Classification Search
CPC ... G06T 11/005; G06T 7/0012; G06T 15/205; G06T 2207/10072; G06T 2207/10116;
(Continued)

(56) References Cited

U.S. PATENT DOCUMENTS 3,502,878 A  3/1970 Stewart
3,863,073 A  1/1975 Wagner
(Continued)

FOREIGN PATENT DOCUMENTS

AU  2014339982 A1 *  5/2016  ............. A61B 6/481
CN  1846622  10/2006
(Continued)

OTHER PUBLICATIONS

M. Ertas, A. Akan, I. Yildirim, A. Dinler and M. Kamasak, "2D versus 3D total variation minimization in digital breast tomosynthesis," 2015 IEEE International Conference on Imaging Systems and Techniques (IST), Macau, 2015, pp. 1-4, doi: 10.1109/IST.2015. 7294553. (Year: 2015).*

(Continued)

*Primary Examiner* — Vu Le
*Assistant Examiner* — Courtney Joan Nelson
(74) *Attorney, Agent, or Firm* — Merchant & Gould P.C.

(57) ABSTRACT

A method for processing breast tissue image data includes processing image data of a patient's breast tissue to generate a high-dimensional grid depicting one or more high-dimensional objects in the patient's breast tissue; determining a probability or confidence of each of the one or more high-dimensional objects depicted in the high-dimensional grid;

(Continued)

and modifying one or more aspects of at least one of the one or more high-dimensional objects based at least in part on its respective determined probability or confidence to thereby generate a lower-dimensional format version of the one or more high-dimensional objects. The method may further include displaying the lower-dimensional format version of the one or more high-dimensional objects in a synthesized image of the patient's breast tissue.

23 Claims, 9 Drawing Sheets

(51) Int. Cl.
  *A61B 6/00* (2006.01)
  *G06T 7/00* (2017.01)
  *G06T 15/20* (2011.01)
(52) U.S. Cl.
  CPC .. *G06T 15/205* (2013.01); *G06T 2207/10072* (2013.01); *G06T 2207/10116* (2013.01); *G06T 2207/30068* (2013.01)
(58) Field of Classification Search
  CPC .......... G06T 2207/30068; G06N 20/00; A61B 6/502
  See application file for complete search history.

(56) References Cited

U.S. PATENT DOCUMENTS

| | | | |
|---|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,668,889 A | 9/1997 | Hara |
| 5,671,288 A | 9/1997 | Wilhelm et al. |
| 5,712,890 A | 1/1998 | Spivey |
| 5,719,952 A | 2/1998 | Rooks |
| 5,735,264 A | 4/1998 | Siczek et al. |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |

(56) References Cited

U.S. PATENT DOCUMENTS

| | | |
|---|---|---|
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 * | 5/2007 | Eberhard ............... A61B 6/463 382/131 |
| 7,245,694 B2 | 7/2007 | Jing et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth et al. |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113681 A1 | 5/2005 | DeFreitas et al. |
| 2005/0113715 A1 | 5/2005 | Schwindt et al. |

(56) References Cited

U.S. PATENT DOCUMENTS

| | | |
|---|---|---|
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0155209 A1 | 7/2006 | Miller et al. |
| 2006/0197753 A1 | 9/2006 | Hotelling |
| 2006/0210131 A1* | 9/2006 | Wheeler, Jr. ......... G06T 11/008 382/128 |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0195882 A1 | 8/2010 | Ren et al. |
| 2010/0208037 A1 | 8/2010 | Sendai |
| 2010/0231522 A1 | 9/2010 | Li |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110576 A1* | 5/2011 | Kreeger ............... G16H 50/20 382/132 |
| 2011/0150447 A1 | 6/2011 | Li |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1* | 1/2012 | Karssemeijer ........ G06T 7/0012 382/131 |
| 2012/0069951 A1 | 3/2012 | Toba |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0189092 A1 | 7/2012 | Jerebko |
| 2012/0194425 A1 | 8/2012 | Buelow |
| 2012/0238870 A1 | 9/2012 | Smith et al. |
| 2012/0293511 A1 | 11/2012 | Mertelmeier |
| 2013/0022165 A1 | 1/2013 | Jang |
| 2013/0044861 A1 | 2/2013 | Muller |
| 2013/0059758 A1* | 3/2013 | Haick .................. B82Y 15/00 977/773 |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1* | 8/2013 | Jerebko ............... G06T 11/006 382/131 |
| 2013/0259193 A1 | 10/2013 | Packard |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0219534 A1 | 8/2014 | Wiemker et al. |
| 2014/0219548 A1 | 8/2014 | Wels et al. |
| 2014/0327702 A1 | 11/2014 | Kreeger et al. |
| 2014/0328517 A1 | 11/2014 | Gluncic |
| 2015/0052471 A1 | 2/2015 | Chen et al. |
| 2015/0061582 A1 | 4/2015 | Smith et al. |
| 2015/0238148 A1 | 8/2015 | Georgescu |
| 2015/0302146 A1 | 10/2015 | Marshall |

(56) References Cited

U.S. PATENT DOCUMENTS

| | | |
|---|---|---|
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman et al. |
| 2016/0140749 A1 | 5/2016 | Erhard |
| 2016/0228034 A1 | 8/2016 | Gluncic |
| 2016/0235380 A1 | 8/2016 | Smith |
| 2016/0367210 A1 | 12/2016 | Gkanatsios |
| 2017/0071562 A1 | 3/2017 | Suzuki |
| 2017/0262737 A1 | 9/2017 | Rabinovich |
| 2018/0047211 A1 | 2/2018 | Chen et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0015173 A1 | 1/2019 | DeFreitas |
| 2019/0043456 A1 | 2/2019 | Kreeger |
| 2019/0290221 A1 | 9/2019 | Smith |
| 2020/0046303 A1 | 2/2020 | DeFreitas |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2022/0005277 A1 | 1/2022 | Chen |
| 2022/0013089 A1 | 1/2022 | Kreeger |
| 2022/0192615 A1 | 6/2022 | Chui |

FOREIGN PATENT DOCUMENTS

| | | | |
|---|---|---|---|
| CN | 202161328 | 3/2012 | |
| CN | 102429678 | 5/2012 | |
| CN | 107440730 | 12/2017 | |
| DE | 102010009295 | 8/2011 | |
| DE | 102011087127 | 5/2013 | |
| EP | 775467 | 5/1997 | |
| EP | 982001 | 3/2000 | |
| EP | 1428473 | 6/2004 | |
| EP | 2236085 | 6/2010 | |
| EP | 2215600 | 8/2010 | |
| EP | 2301432 | 3/2011 | |
| EP | 2491863 | 8/2012 | |
| EP | 1986548 | 1/2013 | |
| EP | 2656789 | 10/2013 | |
| EP | 2823464 | 1/2015 | |
| EP | 2823765 | 1/2015 | |
| EP | 3060132 | 4/2019 | |
| JP | H09-198490 | 7/1997 | |
| JP | H09-238934 | 9/1997 | |
| JP | 10-33523 | 2/1998 | |
| JP | H10-33523 | 2/1998 | |
| JP | 2000-200340 | 7/2000 | |
| JP | 2002-282248 | 10/2002 | |
| JP | 2003-189179 | 7/2003 | |
| JP | 2003-199737 | 7/2003 | |
| JP | 2003-531516 | 10/2003 | |
| JP | 2006-519634 | 8/2006 | |
| JP | 2006-312026 | 11/2006 | |
| JP | 2007-130487 | 5/2007 | |
| JP | 2007-330334 | 12/2007 | |
| JP | 2007-536968 | 12/2007 | |
| JP | 2008-068032 | 3/2008 | |
| JP | 2009-034503 | 2/2009 | |
| JP | 2009-522005 | 6/2009 | |
| JP | 2009-526618 | 7/2009 | |
| JP | 2009-207545 | 9/2009 | |
| JP | 2010-137004 | 6/2010 | |
| JP | 2011-110175 A | 6/2011 | |
| JP | 2012-501750 | 1/2012 | |
| JP | 2012011255 | 1/2012 | |
| JP | 2012-061196 | 3/2012 | |
| JP | 2013-244211 | 12/2013 | |
| JP | 2014-507250 | 3/2014 | |
| JP | 2014-534042 | 12/2014 | |
| JP | 2015-506794 | 3/2015 | |
| JP | 2015-144632 A | 8/2015 | |
| JP | 2016-198197 | 12/2015 | |
| KR | 10-2015-0010515 | 1/2015 | |
| KR | 10-2017-0062839 | 6/2017 | |
| WO | 90/05485 | 5/1990 | |
| WO | 93/17620 | 9/1993 | |
| WO | 94/06352 | 3/1994 | |
| WO | 1997/00649 | 1/1997 | |
| WO | 1998/16903 | 4/1998 | |
| WO | 00/51484 | 9/2000 | |
| WO | 2003/020114 | 3/2003 | |
| WO | 2005051197 | 6/2005 | |
| WO | 2005/110230 | 11/2005 | |
| WO | 2005110230 | 11/2005 | |
| WO | 2005/112767 | 12/2005 | |
| WO | 2005112767 | 12/2005 | |
| WO | 2006/055830 | 5/2006 | |
| WO | 2006/058160 | 6/2006 | |
| WO | 2007/095330 | 8/2007 | |
| WO | 08/014670 | 2/2008 | |
| WO | 2008047270 | 4/2008 | |
| WO | 2008/054436 | 5/2008 | |
| WO | 2009/026587 | 2/2009 | |
| WO | 2010/028208 | 3/2010 | |
| WO | 2010059920 | 5/2010 | |
| WO | 2011008239 | 1/2011 | |
| WO | 2011/043838 | 4/2011 | |
| WO | 2011065950 | 6/2011 | |
| WO | 2011073864 | 6/2011 | |
| WO | 2011091300 | 7/2011 | |
| WO | 2012/001572 | 1/2012 | |
| WO | 2012/068373 | 5/2012 | |
| WO | 2012063653 | 5/2012 | |
| WO | 2012/112627 | 8/2012 | |
| WO | 2012/122399 | 9/2012 | |
| WO | 2013/001439 | 1/2013 | |
| WO | 2013/035026 | 3/2013 | |
| WO | 2013/078476 | 5/2013 | |
| WO | WO-2013123091 A1 * | 8/2013 | ............. A61B 6/466 |
| WO | 2014/149554 | 9/2014 | |
| WO | WO2014/207080 | 12/2014 | |
| WO | WO-2014207080 A1 * | 12/2014 | ............. G06T 15/08 |
| WO | 2015/061582 | 4/2015 | |
| WO | 2015/066650 | 5/2015 | |
| WO | 2015/130916 | 9/2015 | |
| WO | 2016/103094 | 6/2016 | |
| WO | 2016/184746 | 11/2016 | |
| WO | 2018/183548 | 10/2018 | |
| WO | 2018/183550 | 10/2018 | |
| WO | WO2018/183549 | 10/2018 | |
| WO | 2018/236565 | 12/2018 | |

OTHER PUBLICATIONS

B. E. Caroline and N. Vaijayanthi, "Computer aided detection of masses in digital breast tomosynthesis: A review," 2012 International Conference on Emerging Trends in Science, Engineering and Technology (INCOSET), Tiruchirappalli, 2012, pp. 186-191, doi: 10.1109/INCOSET.2012.6513903 (Year: 2012).*

International Search Report and Written Opinion dated Jun. 8, 2018 for PCT application No. PCT/US2018/024912, applicant Hologic, Inc., 10 pages.

Non-Final Office Action for U.S. Appl. No. 16/497,767 dated Feb. 19, 2021.

U.S. Appl. No. 16/497,767, Office Action dated Jul. 16, 2021, 26 pages.

PCT International Preliminary Report on Patentability in International Application PCT/US2018/024912, dated Oct. 10, 2019, 7 pages.

(56) References Cited

OTHER PUBLICATIONS

"Filtered Back Projection", (Nygren), published May 8, 2007, URL: http://web.archive.org/web/19991010131715/http://www.owlnet.rice.edu/~elec539/Projects97/cult/node2.html, 2 pgs.
Berg, WA et al., "Combined screening with ultrasound and mammography vs mammography alone in women at elevated risk of breast cancer", JAMA 299:2151-2163, 2008.
Carton, AK, et al., "Dual-energy contrast-enhanced digital breast tomosynthesis—a feasibility study", BR J Radiol. Apr. 2010;83 (988):344-50.
Chen, SC, et al., "Initial clinical experience with contrast-enhanced digital breast tomosynthesis", Acad Radio. Feb. 2007 14(2):229-38.
Diekmann, F., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain, C., et al., "Contrast-enhanced digital mammography", Eur J Radiol. 2009; 69:34-42.
Freiherr, G., "Breast tomosynthesis trials show promise", Diagnostic Imaging—San Francisco 2005, V27; N4:42-48.
Giger et al. "Development of a smart workstation for use in mammography", in Proceedings of SPIE, vol. 1445 (1991), p. 101103; 4 pages.
Giger et al., "An Intelligent Workstation for Computer-aided Diagnosis", in RadioGraphics, May 1993, 13:3 pp. 647-656; 10 pages.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Jochelson, M., et al., "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Kopans, et al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lewin,JM, et al., Dual-energy contrast-enhanced digital subtraction mammography: feasibility. Radiology 2003; 229:261-268.
Lindfors, KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Poplack, SP, et al., Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", AM J Clin Pathol. Nov. 2004 122(5):696-703.
"Supersonic to feature Aixplorer Ultimate at ECR", AuntiMinnie.com, 3 pages (Feb. 2018).
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Dromain, Clarisse et al., "Dual-energy contrast-enhanced digital mammography: initial clinical results", European Radiology, Sep. 14, 2010, vol. 21, pp. 565-574.
Reynolds, April, "Stereotactic Breast Biopsy: A Review", Radiologic Technology, vol. 80, No. 5, Jun. 1, 2009, pp. 447M-464M, XP055790574.
Fischer Imaging Corp, Mammotest Plus manual on minimally invasive breast biopsy system, 2002, 8 pages. (Reference labeled D13 in 01 Opposition).
Fischer Imaging Corporation, Installation Manual, MammoTest Family of Breast Biopsy Systems, 86683G, 86684G, P-55957-IM, Issue 1, Revision 3, Jul. 2005, 98 pages. (Reference labeled D12 in 01 Opposition).
Fischer Imaging Corporation, Operator Manual, MammoTest Family of Breast Biopsy Systems, 86683G, 86684G, P-55956-OM, Issue 1, Revision 6, Sep. 2005, 258 pages. (Reference labeled D11 in 01 Opposition).
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009. (Reference labeled D10 in 01 Opposition).
E. Shaw de Paredes et al., "Interventional Breast Procedure", published Sep./Oct. 1998 in Curr Probl Diagn Radiol, pp. 138-184. (D15 in oppo).
Burbank, Fred, "Stereotactic Breast Biopsy: Its History, Its Present, and Its Future", published in 1996 at the Southeastern Surgical Congress, 24 pages.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages. (Reference labeled D10 in 0020 Opposition).
Samani, A. et al., "Biomechanical 3-D Finite Element Modeling of the Human Breast Using MRI Data", 2001, IEEE Transactions on Medical Imaging, vol. 20, No. 4, pp. 271-279.
Yin, H.M., et al., "Image Parser: a tool for finite element generation from three-dimensional medical images", BioMedical Engineering Online. 3:31, pp. 1-9, Oct. 1, 2004.
Sakic et al., "Mammogram synthesis using a 3D simulation. I. breast tissue model and image acquisition simulation" Medical Physics. 29, pp. 2131-2139 (2002).
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
Al Sallab et al., "Self Learning Machines Using Deep Networks", Soft Computing and Pattern Recognition (SoCPaR), 2011 Int'l. Conference of IEEE, Oct. 14, 2011, pp. 21-26.
Ghiassi, M. et al., "A Dynamic Architecture for Artificial Networks", Neurocomputing, vol. 63, Aug. 20, 2004, pp. 397-413.
Chan, Heang-Ping et al., "ROC Study of the effect of stereoscopic imaging on assessment of breast lesions," Medical Physics, vol. 32, No. 4, Apr. 2005, 1001-1009.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

(56) References Cited

OTHER PUBLICATIONS

Pediconi, "Color-coded automated signal intensity-curve for detection and characterization of breast lesions: Preliminary evaluation of new software for MR-based breast imaging," International Congress Series 1281 (2005) 1081-1086.
eFilm Mobile HD by Merge Healthcare, web site: http://itunes.apple.com/bw/app/efilm-mobile-hd/id405261243?mt=8, accessed on Nov. 3, 2011 (2 pages).
eFilm Solutions, eFilm Workstation (tm) 3.4, website: http://estore.merge.com/na/estore/content.aspx?productID=405, accessed on Nov. 3, 2011 (2 pages).
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.
Conner, Peter, "Breast Response to Menopausal Hormone Therapy—Aspects on Proliferation, apoptosis and Mammographic Density", 2007 Annals of Medicine, 39;1, 28-41.
Glick, Stephen J., "Breast CT", Annual Rev. Biomed. Eng., 2007, 9;501-26.
Metheany, Kathrine G. et al., "Characterizing anatomical variability in breast CT images", Oct. 2008, Med. Phys. 35 (10); 4685-4694.
Dromain, Clarisse, et al., "Evaluation of tumor angiogenesis of breast carcinoma using contrast-enhanced digital mammography", AJR: 187, Nov. 2006, 16 pages.
Zhao, Bo, et al., "Imaging performance of an amorphous selenium digital mammography detector in a breast tomosynthesis system", May 2008, Med. Phys 35(5); 1978-1987.
Mahesh, Mahadevappa, "AAPM/RSNA Physics Tutorial for Residents—Digital Mammography: An Overview", Nov.-Dec. 2004, vol. 24, No. 6, 1747-1760.
Zhang, Yiheng et al., "A comparative study of limited-angle cone-beam reconstruction methods for breast tomosythesis", Med Phys., Oct. 2006, 33(10): 3781-3795.
Sechopoulos, et al., "Glandular radiation dose in tomosynthesis of the breast using tungsten targets", Journal of Applied Clinical Medical Physics, vol. 8, No. 4, Fall 2008, 161-171.
Wen, Junhai et al., "A study on truncated cone-beam sampling strategies for 3D mammography", 2004, IEEE, 3200-3204.
Ijaz, Umer Zeeshan, et al., "Mammography phantom studies using 3D electrical impedance tomography with numerical forward solver", Frontiers in the Convergence of Bioscience and Information Technologies 2007, 379-383.
Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.
Varjonen, Mari, "Three-Dimensional Digital Breast Tomosynthesis in the Early Diagnosis and Detection of Breast Cancer", IWDM 2006, LNCS 4046, 152-159.
Taghibakhsh, f. et al., "High dynamic range 2-TFT amplified pixel sensor architecture for digital mammography tomosynthesis", IET Circuits Devices Syst., 2007, 1(10, pp. 87-92.
Chan, Heang-Ping et al., "Computer-aided detection system for breast masses on digital tomosynthesis mammograms: Preliminary Experience", Radiology, Dec. 2005, 1075-1080.

* cited by examiner

SYSTEM AND METHOD FOR SYNTHESIZING LOW-DIMENSIONAL IMAGE DATA FROM HIGH-DIMENSIONAL IMAGE DATA USING AN OBJECT GRID ENHANCEMENT

RELATED APPLICATIONS DATA

The present application is a National Phase entry under 35 U.S.C § 371 of International Patent Application No. PCT/US2018/024912, having an international filing date of Mar. 28, 2018, which claims the benefit under 35 U.S.C. § 119 to U.S. Provisional Patent Application Ser. No. 62/479,008, filed Mar. 30, 2017, which is incorporated by reference in its entirety into the present application.

FIELD

The presently disclosed inventions relate to systems and methods for processing and displaying breast tissue images, and in particular to representing high-dimensional (e.g., 3D) structures present in breast tissue image data with a high-dimensional object grid, and then reducing the high-dimensional data to a low-dimensional (e.g., 2D) format version that can be incorporated within a synthesized image to be displayed to a medical professional.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional images of the breast using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being mathematically reconstructed on planes typically parallel to the imaging detector. The reconstructed tomosynthesis slices reduce or eliminate the problems caused by tissue overlap and structure noise present in single slice, two-dimensional mammography imaging, by permitting a user (e.g., a radiologist or other medical professional) to scroll through the image slices to view only the structures in that slice.

Imaging systems such as tomosynthesis systems have recently been developed for breast cancer screening and diagnosis. In particular, Hologic, Inc. (hologic.com) has developed a fused, multimode mammography/tomosynthesis system that acquires one or both types of mammogram and tomosynthesis images, either while the breast remains immobilized or in different compressions of the breast. Other companies have introduced systems that include tomosynthesis imaging; e.g., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may optionally be displayed along with tomosynthesis projection or reconstructed images, in order to assist in screening and diagnosis.

A 2D synthesized image is designed to provide a concise representation of the 3D reconstruction slices, including any clinically important and meaningful information, such as abnormal lesions and normal breast structures, while representing in relevant part a traditional 2D image. There are many different types of lesions and breast structures, which may be defined as different types of image objects having different characteristics. For any given image object visible in the 3D volume data, it is important to maintain and enhance the image characteristics (e.g., micro-calcifications, architectural distortions, etc.) as much as possible onto the 2D synthesized image. Further, when representing multiple identified objects on the 2D synthesized image, the synthesized image may appear crowded and visually confusing. Accordingly, there exists a need for more effectively processing, synthesizing and displaying breast image data.

SUMMARY

In one embodiment of the disclosed inventions, a method for processing breast tissue image data includes obtaining image data of a patient's breast tissue; processing the image data to generate a high-dimensional grid depicting one or more high-dimensional objects in the patient's breast tissue; determining a probability or confidence of each of the one or more high-dimensional objects depicted in the high-dimensional grid; and generating a lower-dimensional format version of the one or more high-dimensional objects for display in a synthesized image of the patient's breast tissue.

These and other aspects and embodiments of the disclosed inventions are described in more detail below, in conjunction with the accompanying figures.

BRIEF DESCRIPTION OF THE FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
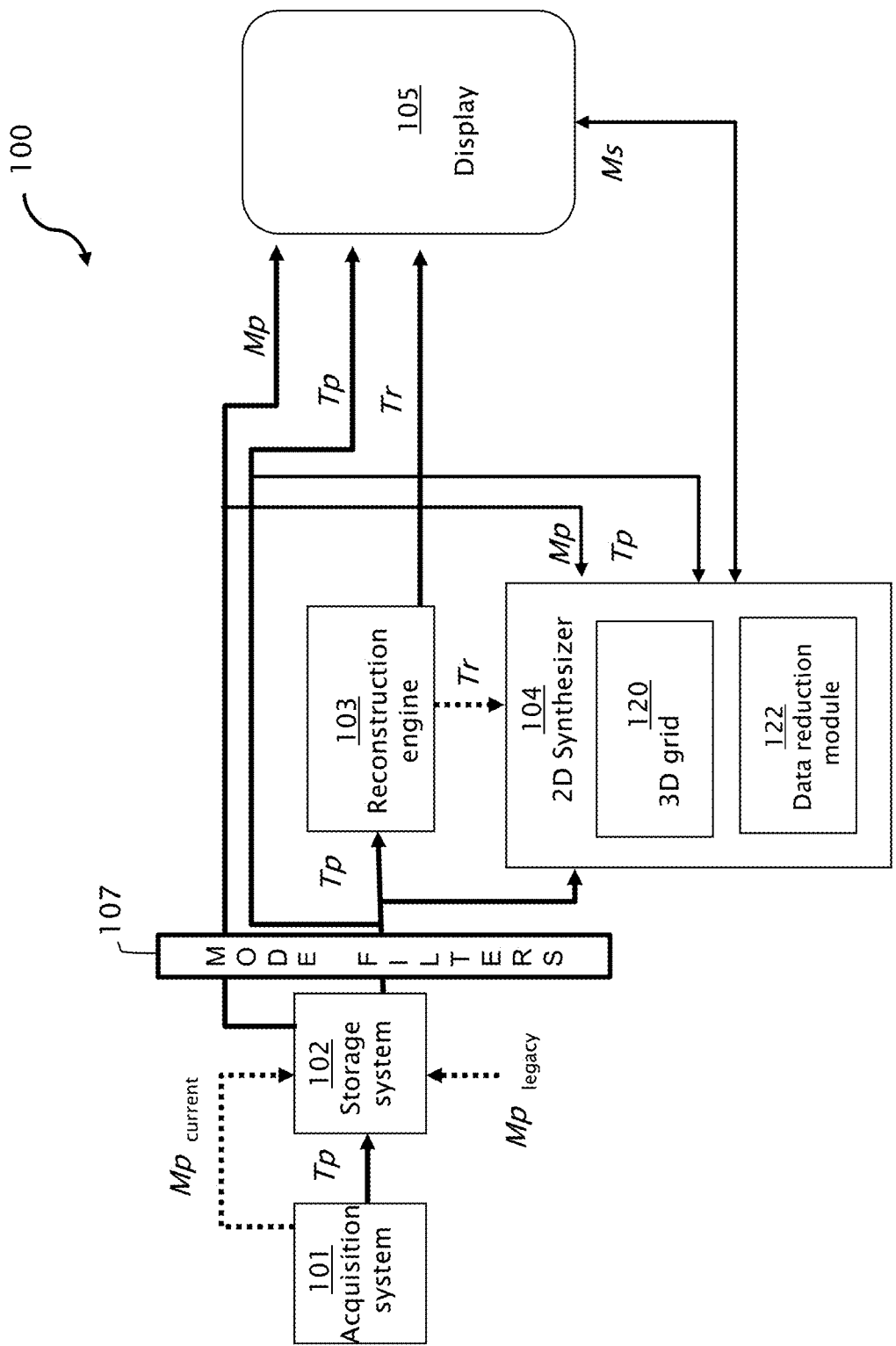
FIG. 1 is a block diagram illustrating the flow of data through an exemplary breast image acquisition and processing system in accordance with embodiments of the disclosed inventions.

All numeric values are herein assumed to be modified by the terms "about" or "approximately," whether or not explicitly indicated, wherein the terms "about" and "approximately" generally refer to a range of numbers that one of skill in the art would consider equivalent to the recited value (i.e., having the same function or result). In some instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the disclosed inventions, which is defined only by the appended claims and their equivalents. In addition, an illustrated embodiment of the disclosed inventions needs not have all the aspects or advantages shown. For example, an aspect or an advantage described in conjunction with a particular embodiment of the disclosed inventions is not necessarily limited to that embodiment and can be practiced in any other embodiments even if not so illustrated.

For the following defined terms and abbreviations, these definitions shall be applied throughout this patent specification and the accompanying claims, unless a different definition is given in the claims or elsewhere in this specification:

An "acquired image" refers to an image generated while visualizing a patient's tissue. Acquired images can be generated by radiation from a radiation source impacting on a radiation detector disposed on opposite sides of a patient's tissue, as in a conventional mammogram.

A "reconstructed image" refers to an image generated from data derived from a plurality of acquired images. A reconstructed image simulates an acquired image not included in the plurality of acquired images.

A "synthesized image" refers to an artificial image generated from data derived from a plurality of acquired and/or reconstructed images. A synthesized image includes elements (e.g., objects and regions) from the acquired and/or reconstructed images, but does not necessarily correspond to an image that can be acquired during visualization. Synthesized images are constructed analysis tools.

An "Mp" image is a conventional mammogram or contrast enhanced mammogram, which are two-dimensional (2D) projection images of a breast, and encompasses both a digital image as acquired by a flat panel detector or another imaging device, and the image after conventional processing to prepare it for display (e.g., to a health professional), storage (e.g., in the PACS system of a hospital), and/or other use.

A "Tp" image is an image that is similarly two-dimensional (2D), but is acquired at a respective tomosynthesis angle between the breast and the origin of the imaging x-rays (typically the focal spot of an x-ray tube), and encompasses the image as acquired, as well as the image data after being processed for display, storage, and/or other use.

A "Tr" image is a type (or subset) of a reconstructed image that is reconstructed from tomosynthesis projection images Tp, for example, in the manner described in one or more of U.S. Pat. Nos. 7,577,282, 7,606,801, 7,760,924, and 8,571,289, the disclosures of which are fully incorporated by reference herein in their entirety, wherein a Tr image represents a slice of the breast as it would appear in a projection x-ray image of that slice at any desired angle, not only at an angle used for acquiring Tp or Mp images.

An "Ms" image is a type (or subset) of a synthesized image, in particular, a synthesized 2D projection image, which simulates mammography images, such as craniocaudal (CC) or mediolateral oblique (MLO) images, and is constructed using tomosynthesis projection images Tp, tomosynthesis reconstructed images Tr, or a combination thereof. Ms images may be provided for display to a health professional or for storage in the PACS system of a hospital or another institution. Examples of methods that may be used to generate Ms images are described in the above-incorporated U.S. Pat. Nos. 7,760,924 and 8,571,289.

It should be appreciated that Tp, Tr, Ms and Mp image data encompasses information, in whatever form, that is sufficient to describe the respective image for display, further processing, or storage. The respective Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to X-rays of corresponding volumes in the breast, i.e., voxels or columns of tissue. In a preferred embodiment, the geometry of the tomosynthesis images (Tr and Tp) and mammography images (Ms and Mp) are matched to a common coordinate system, as described in U.S. Pat. No. 7,702,142. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

In order to ensure that a synthesized 2D image displayed to an end-user (e.g., an Ms image) includes the most clinically relevant information, it is necessary to detect and identify three-dimensional (3D) objects, such as malignant breast mass, tumors, etc., within the breast tissue. In accordance with the inventions disclosed and described herein, this information may be used to create a high-dimensional grid, e.g., a 3D grid, that helps create a more accurate and enhanced rendering of the most important features in the synthesized 2D image. The high-dimensional object grid may then be used to collapse the most clinically-significant information pertaining to the identified objects to a 2D format onto one or more synthesized 2D images. Various data reduction techniques may be applied to the identified 3D objects to ensure that the most clinically-significant objects are emphasized, and less significant objects are omitted and/or de-emphasized. Additionally, or alternatively, data reduction techniques are applied to ensure that significant features of a 3D object are enhanced, while less significant features of the 3D object are de-emphasized, especially when two objects are competing for display and prominence on the one or more 2D synthesized images. Thus, as disclosed and described herein, a 3D object grid is utilized, i.e., as a component of an algorithm, for reducing high-dimensional data (e.g., 3D tomosynthesis image data) to low-dimensional data (e.g. a 2D synthesized image).

FIG. 1 illustrates the flow of data in an exemplary image generation and display system 100, which incorporates each of synthesized image generation, object identification, and display technology. It should be understood that, while FIG. 1 illustrates a particular embodiment of a flow diagram with certain processes taking place in a particular serial order or in parallel, the claims and various other embodiments described herein are not limited to the performance of the image processing steps in any particular order, unless so specified.

More particularly, the image generation and display system 100 includes an image acquisition system 101 that acquires tomosynthesis image data for generating Tp images of a patient's breasts, using the respective three-dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend "$Mp_{legacy}$" in FIG. 1) in a storage device 102, which is preferably a DICOM-compliant Picture Archiving and Communication System (PACS) storage device. Following acquisition, the tomosynthesis projection images Tp may also be transmitted to the storage device 102 (as shown in FIG. 1). The storage device 102 may further store a library of known 3D objects that may be used to identify significant 3D image patterns to the end-user. In other embodiments, a separate dedicated storage device (not shown) may be used to store the library of known 3D objects with which to identify 3D image patterns or objects.

The Tp images are transmitted from either the acquisition system 101, or from the storage device 102, or both, to a computer system configured as a reconstruction engine 103 that reconstructs the Tp images into reconstructed image "slices" Tr, representing breast slices of selected thickness and at selected orientations, as disclosed in the above-incorporated patents and applications.

Mode filters 107 are disposed between image acquisition and image display. The filters 107 may additionally include customized filters for each type of image (i.e., Tp, Mp, and Tr images) arranged to identify and highlight certain aspects of the respective image types. In this manner, each imaging mode can be tuned or configured in an optimal way for a specific purpose. For example, filters programmed for recognizing objects across various 2D image slices may be applied in order to detect image patterns that may belong to a particular high-dimensional object. The tuning or configuration may be automatic, based on the type of the image, or may be defined by manual input, for example through a user interface coupled to a display. In the illustrated embodiment of FIG. 1, the mode filters 107 are selected to highlight particular characteristics of the images that are best displayed in respective imaging modes, for example, geared towards identifying objects, highlighting masses or calcifications, identifying certain image patterns that may be constructed into a 3D object, or for creating 2D synthesized images (described below). Although FIG. 1 illustrates only one mode filter 107, it should be appreciated that any number of mode filters may be utilized in order to identify structures of interest in the breast tissue.

The imaging and display system 100 further includes a 2D image synthesizer 104 that operates substantially in parallel with the reconstruction engine 103 for generating 2D synthesized images using a combination of one or more Tp, Mp, and/or Tr images. The 2D image synthesizer 104 consumes a set of input images (e.g., Mp, Tr and/or Tp images), determines a set of most relevant features from each of the input images, and outputs one or more synthesized 2D images. The synthesized 2D image represents a consolidated synthesized image that condenses significant portions of various slices onto one image. This provides an end-user (e.g., medical personnel, radiologist, etc.) with the most clinically-relevant image data in an efficient manner, and reduces time spent on other images that may not have significant data.

One type of relevant image data to highlight in the synthesized 2D images would be relevant objects found across one or more Mp, Tr and/or Tp images. Rather than simply assessing image patterns of interest in each of the 2D image slices, it may be helpful to determine whether any of the 2D image patterns of interest belong to a larger high-dimensional structure, and if so, to combine the identified 2D image patterns into a higher-dimensional structure. This approach has several advantages, but in particular, by identifying high-dimensional structures across various slices/depths of the breast tissue, the end-user may be better informed as to the presence of a potentially significant structure that may not be easily visible in various 2D slices of the breast.

Further, instead of identifying similar image patterns in two 2D slices (that are perhaps adjacent to each other), and determining whether or not to highlight image data from one or both of the 2D slices, identifying both image patterns as belonging to the same high-dimensional structure may allow the system to make a more accurate assessment pertaining to the nature of the structure, and consequently provide significantly more valuable information to the end-user. Also, by identifying the high-dimensional structure, the structure can be more accurately depicted on the synthesized 2D image. Yet another advantage of identifying high-dimensional structures within the various captured 2D slices of the breast tissue relates to identifying a possible size/scope of the identified higher-dimensional structure. For example, once a structure has been identified, previously unremarkable image patterns that are somewhat proximate to the high-dimensional structure may now be identified as belonging to the same structure. This may provide the end-user with an indication that the high-dimensional structure is increasing in size/scope.

To this end, the 2D image synthesizer 104 generates high-dimensional object grids 120 (e.g., 3D object grids) comprising one or more high-dimensional structures (e.g., 3D objects) present in the patient's breast tissue. Several techniques may be used to construct 3D object grids 120 that identify various objects in the breast tissue. It should be appreciated that this disclosure is not limited to 3D objects and/or structures, and may refer to even higher-dimensional structures, but for simplicity, the remaining disclosure will refer to 3D objects populated in a 3D object grid 120.

In one or more embodiments, the 3D object grid 120 is in the form of a 3D (volumetric) coordinate space representing a patient's breast mass, and identifies a location, identity, size, scope, and/or other characteristics of any objects or structures found in the breast mass. Examples of such objects or structures include calcifications, spiculated lesions, benign tumors, irregular masses, dense objects, etc.

In one or more embodiments, the end-user (e.g., a medical professional such as a radiologist) can access and interact with the 3D object grid 120. In other embodiments, the 3D object grid 120 is solely used by the system processor for constructing synthesized 2D images, and the end-user may not be aware of, or have access to, the 3D object grid 120.

In accordance with the disclosed embodiments, the 2D image synthesizer 104 also includes a data reduction module 122 configured to reduce the high-dimensional data populated in the 3D object grid 120 to a lower-dimensional format suitable for representation in a 2D synthesized image. The data reduction module 122 evaluates the various objects of the 3D object grid 120, and determines what objects (or what portions of objects) should be enhanced or emphasized in a final 2D synthesized image to be displayed to the end-user. For example, a clinically significant object and a routine background breast tissue object may have regions of overlap, in which case the data reduction module 122 is preferably configured to de-emphasize portions of the background breast tissue in order to highlight the clinically significant object. Further details on various data reduction techniques that may be employed by the data reduction module 122 are described below.

The synthesized 2D images may be viewed at a display system 105. The reconstruction engine 103 and 2D image synthesizer 104 are preferably connected to a display system 105 via a fast transmission link. The display system 105 may be part of a standard acquisition workstation (e.g., of acquisition system 101), or of a standard (multi-display) review station (not shown) that is physically remote from the acquisition system 101. In some embodiments, a display connected via a communication network may be used, for example, a display of a personal computer or of a so-called tablet, smart phone or other hand-held device. In any event, the display 105 of the system is preferably able to display respective Ms, Mp, Tr, and/or Tp images concurrently, e.g., in separate side-by-side monitors of a review workstation, although the invention may still be implemented with a single display monitor, by toggling between images.

Thus, the imaging and display system 100, which is described as for purposes of illustration and not limitation, is capable of receiving and selectively displaying tomosynthesis projection images Tp, tomosynthesis reconstruction images Tr, synthesized mammogram images Ms, and/or mammogram (including contrast mammogram) images Mp, or any one or sub combination of these image types. The system 100 employs software to convert (i.e., reconstruct) tomosynthesis images Tp into images Tr, software for synthesizing mammogram images Ms, software for decomposing 3D objects, software for creating feature maps and object maps. An object of interest or feature in a source image may be considered a 'most relevant' feature for inclusion in a 2D synthesized image based upon the application of the object maps along with one or more algorithms and/or heuristics, wherein the algorithms assign numerical values, weights or thresholds, to pixels or regions of the respective source images based upon identified/detected objects and features of interest within the respective region or between features. The objects and features of interest may include, for example, spiculated lesions, calcifications, and the like.

Figure 2:
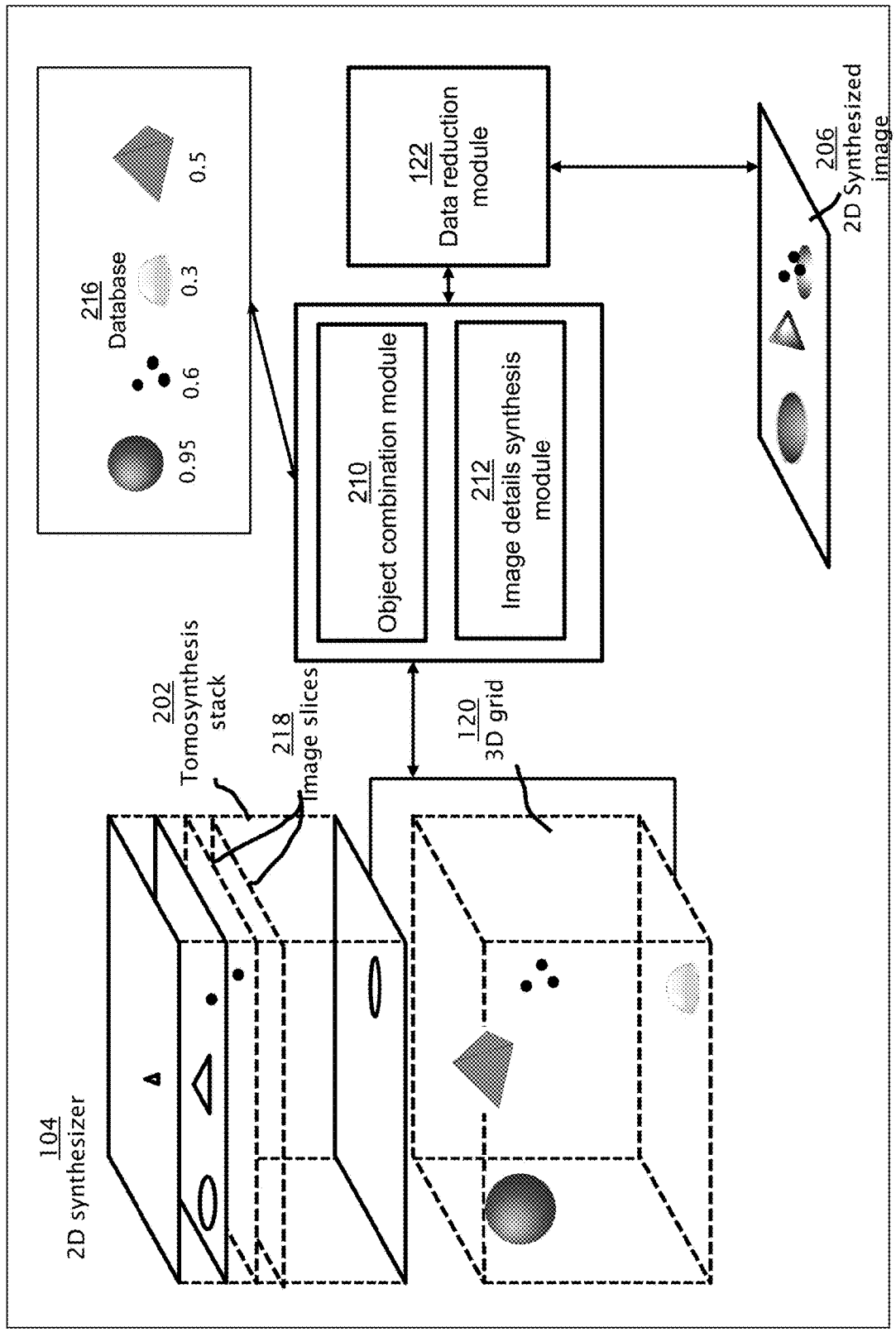
FIG. 2 is a block diagram illustrating the flow of data through a 2D synthesizer employing a 3D object grid and various modules that reduce objects of the grid to a 2D format for display.

FIG. 2 illustrates the 2D image synthesizer 104 in further detail. As discussed above, various image slices 218 of a tomosynthesis data set (or "stack") 202 (e.g., filtered and/or unfiltered Mp, Tr and/or Tp images of a patient's breast tissue) are input into the 2D image synthesizer 104, and then processed to determine portions of the images to highlight in a synthesized 2D image that will be displayed on the display 105. The image slices 218 may be consecutively-captured cross-sections of a patient's breast tissue. Or, the image slices 218 may be cross-sectional images of the patient's breast tissue captured at known intervals. The tomosynthesis image stack 202 comprising the image slices 218 may be forwarded to the 2D image synthesizer 104, which evaluates each of the source images in order to (1) identify various types of objects (Tr) for possible inclusion in one or more 2D synthesized images, and/or (2) identify respective pixel regions in the images that contain the identified objects.

As shown in the illustrated embodiment, the tomosynthesis stack 202 comprises a plurality of images 218 taken at various depths/cross-sections of the patient's breast tissue. Some of the images 218 in the tomosynthesis stack 202 comprise 2D image patterns. Thus, the tomosynthesis stack 202 comprises a large number of input images containing various image patterns within the images of the stack.

For example, while the tomosynthesis stack 202 may comprise one hundred images 218 captured at various depths/cross sections of the patient's breast tissue, only a few of the images 218 may include any information of significance. Also, it should be noted that the tomosynthesis stack 202 contains 2D image patterns when viewed at differing z-dimension (depth) locations of the otherwise same x, y locations in the image slices 218, but it may be difficult to determine the 3D structures based only on the various individual images, each representing a finite cross-sectional image of the breast tissue. However, the tomosynthesis stack 202 may be effectively utilized to create the 3D object grid 120. In any event, for purposes of this patent specification, it is assumed that the 3D object grid 120 is constructed by any means, including but not limited to being created from the tomosynthesis stack 202.

The 3D object grid 120 may be considered a 3D volumetric coordinate space representing a patient's breast mass. Rather than depicting 2D image patterns at various image slices, the 3D object grid 120 preferably depicts any identified 3D objects in the entire mass (or portion thereof) that represents the patient's breast tissue. The 3D object grid 120 provides fuller detail regarding various objects in the breast mass as compared to the tomosynthesis stack 202. For example, the 3D object grid 120 may use simulation techniques to infer a shape of the 3D object, even though an image slice may not have necessarily been reconstructed at every cross-sectional depth covering the respective 3D object.

The 3D object grid 120 may comprise one or more objects, as shown in the illustrated embodiment. It should be appreciated that these objects may be predefined objects that the system has been trained to identify. However, even in healthy breast tissue that does not necessarily comprise any abnormal objects or structures, the target object recognition/enhancement modules may identify a breast background object. For example, all breast linear tissue and density tissue structures can be displayed as the breast background object. In other embodiments, "healthy" objects such as spherical shapes, oval shapes, etc., may simply be identified through one or more target object recognition/enhancement modules 210. These identified 3D objects may then be displayed on the 2D synthesized image 206; of course, out of all identified 2D objects, more clinically-significant objects may be prioritized and/or enhanced when displaying the respective object on the 2D synthesized image, as will be discussed in further detail below.

In one or more embodiments, the 2D synthesizer 104 utilizes both the tomosynthesis image stack 202 along with the created 3D object grid 120 in order to merge the relevant features into one or more 2D synthesized images 206. As shown in the 2D synthesized image, the 3D objects identified in the 3D object grid 120 are collapsed into a 2D format, but provide more detail when compared to individual image slices of the tomosynthesis image stack 202. Further, although several objects, as shown in the tomosynthesis image stack 202 overlap in the z direction, identifying them as separate 3D objects allows the system to depict both objects clearly and efficiently. Simply utilizing legacy image recognizing techniques on the tomosynthesis image stack 202 may or may not necessarily provide such an accurate synthesized 2D image 206. To explain, if there is overlap in the z direction of two structures, the two structures are essentially competing with each other for display on the 2D synthesized image 206. Thus, important aspects of both structures may be compromised. Or, only one of the two structures may be highlighted at all in the 2D synthesized image 206. Or, in yet another scenario, the 2D synthesized image may depict both structures as one amorphous structure such that an important structure goes entirely undetectable for the end-user.

It will be appreciated that identifying 3D objects as separate objects with predefined types in the 3D object grid 120 allows the system to depict the structures more accurately on the 2D synthesized image 206, and allows for various objects to be depicted simultaneously, even if there is an overlap of various objects in the coordinate space. Thus, utilizing the 3D object grid 120 has many advantages for producing a more accurate and visually-effective 2D synthesized image 206.

In one or more embodiments, data from the tomosynthesis stack 202 and the 3D object grid 120 are processed by one or more modules to produce the 2D synthesized image 206. More particularly, an object combination module 210 may be configured to identify the various objects of the 3D object grid 120, and determine a most optimal method to collapse all the objects on a 2D plane/format. For example, the object combination module 210 may determine x and y coordinates for the plurality of objects and determine whether there are overlaps between multiple objects to be displayed on the 2D synthesized image 206. In some embodiments, the object combination module 210 may further be configured to determine which of the identified objects should be displayed on the 2D synthesized image 206. This may be achieved through a training (or a "learning library" type) database 216 that stores an identity of various objects and associated weights of respective objects. The training database becomes more knowledgeable with the processing of each new patent breast image data, as the system derives 3D object models and (subsequently) detection mechanisms from this database, which will grow to include various samples of the same types of objects.

After the 3D objects are detected, then the next step is to utilize this same knowledge in synthesizing the 2D image. Since there may be many different types (or categories) of 3D objects, the weighting mechanism helps to combine the objects in the synthesis/data reduction process. For example, a dense spherical object may be weighed higher than a calcification (weighed 0.95 and 0.6 respectively in the illustrated embodiment), such that the dense spherical object may be enhanced to a greater degree as compared to a calcification. If the weight of an object is close to zero, the object combination module 210 may determine that the object need not be displayed at all, in some embodiments.

In one or more embodiments, an image details synthesis module 212 may be configured to determine what 3D objects or what areas within a 3D object should be emphasized in the 2D synthesized image 206. For example, if there is an overlap between two objects, the image details synthesis module 212 may emphasize portions of both objects, and de-emphasize other portions of both objects such that both objects are clearly viewable on the 2D synthesized image. By manipulating aspects of both objects, the end-user may be able to identify both objects clearly. It should be appreciated that without this manipulation, both objects may simply be overlayed on top of each other, such that one object may simply be masked out and missed by the end-user.

Figure 3:
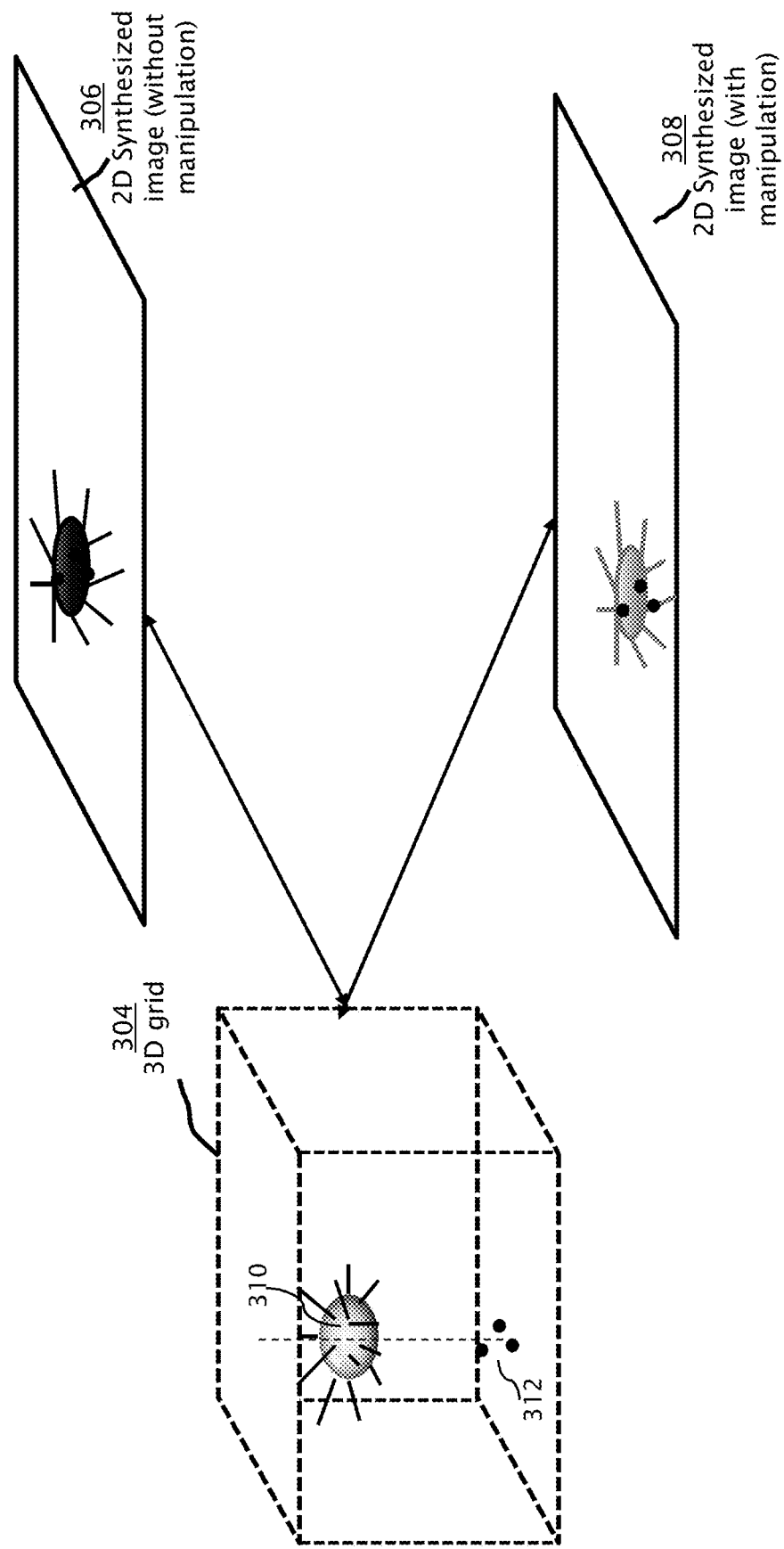
FIG. 3 illustrates a first synthesized image formed from the 3D object grid of FIG. 2 without manipulating overlapping objects, and a second synthesized image formed from the same 3D object grid, but with manipulation of overlapping objects.

For example, the 3D object grid 120 may include a calcification area and a spiculated lesion that overlap in the z direction. Without any specially designed image synthesis, a collapsed 2D format of the spiculated lesion and a collapsed 2D format of the calcification would be displayed on top of each other. Assuming the spiculated mass is larger, the spiculated mass may envelop the calcification entirely such that it is not visible to the end-user. Instead, the image details synthesis module 212 may emphasize the outline of the center portion of the spiculated mass, while deemphasizing the middle portion of the spiculated mass such that the calcification area is visible. This image manipulation allows the end-user a clearer picture of significant objects on the 2D synthesized image 206. FIG. 3, described below, illustrates this system feature in further detail.

In some embodiments, the image details synthesis module 212 may comprise several algorithms and/or heuristics that are programmed with rules to determine what parts of an object to emphasize/de-emphasize based on the object database 216. For example, each object in the database 216 may correspond to metadata that defines most prominent and least-prominent features of the respective object. This metadata may be used by the various algorithms to determine which objects and/or which parts of objects to emphasize in the 2D synthesized images 206. By way of another example, a difference in weight between two overlapping objects may be calculated in order to determine whether both objects should be displayed. If the difference in weight is smaller than a predetermined threshold value, both objects may be displayed, but the assigned weight may be used to determine which of the two objects to emphasize over the other. However, if the difference in weight is larger than the predetermined threshold value, only the object corresponding to the higher weight may be displayed at all. For example, if a dense spherical mass and calcification area are competing for display (difference of 0.35 in weight as per the illustrated embodiment) and the threshold value is set at 0.4, both objects may be displayed, but the spiculated mass (or parts of the spiculated mass) may be highlighted relative to the calcification area. However, if the spiculated mass and a benign semi-spherical mass are overlapping (difference of 0.65 in weight as per the illustrated embodiment), only the dense spherical mass may be displayed at all. Other rules may be defined to allow the system to modify the objects or portions thereof.

As noted above (and in FIG. 1), the 2D image synthesizer 104 further includes a data reduction engine 122 configured to receive the data input from the respective image details synthesis module 212 and object combination module 210, and to reduce any 3D objects identified therein into a low level 2D format that may be inserted into the 2D synthesized image 206. In particular, and as described in further detail herein, the data reduction engine 122 accurately reduces the identified high-dimensional object of the 3D object grid 120 to a 2D format based on input received from the image details synthesis module 212, the database 216 and the object combination module 210.

FIG. 3 depicts an example of how the 3D object grid may be utilized to generate the 2D synthesized images. In the illustrated embodiment, 3D object grid 304 includes at least two 3D objects: a spiculated mass 310, and a calcification area 312. When consulting a database, the object combination module may determine that both objects are important to display in the 2D synthesized image, the spiculated mass 310 being more significant than the calcification. However, since both 3D objects 310 and 312 overlap in the z direction, the images may have to be manipulated such that both objects are still optimally displayed on the 2D synthesized image. In particular, the 2D synthesized image 306 displays a synthesized image that does not use any image manipulation techniques described in this disclosure. As shown in 2D synthesized image 306, both 3D objects 310 and 312 are competing to be displayed, and neither object is displayed very clearly. More specifically, the calcification 312 is barely visible in the 2D synthesized image 306.

By contrast, referring to 2D synthesized image 308, the techniques described with respect to FIG. 2 are utilized in order to determine what parts of the respective 3D object should be emphasized and de-emphasized such that both objects are clearly discernible in the 2D synthesized image. More particularly, although spiculated mass 310 is more significant than the calcification 312, the center portion of the spiculated mass 310 is slightly de-emphasized such that the calcification area is clearly visible. Similarly, it may be determined that the linear lines radiating from the center portion should be emphasized such that the end-user understands a size or scope of the spiculated mass. In light of the modified image corresponding to the spiculated mass 310, the calcification 312 is now visible even though both objects overlap. Thus, as shown in FIG. 3, the 2D synthesized image 308 provides more details about both 3D objects 310 and 312 when compared to 2D synthesized image 306.

FIGS. 4A-4D depict exemplary embodiments of displaying various objects of the 3D object grid, while preserving clinically-significant information. In particular, the collapsing of a 3D object into the 2D synthesized image may be achieved by the respective object combination module, image synthesis module and data reduction module that work together to display as much clinically-significant information as possible.

Figure 4A:
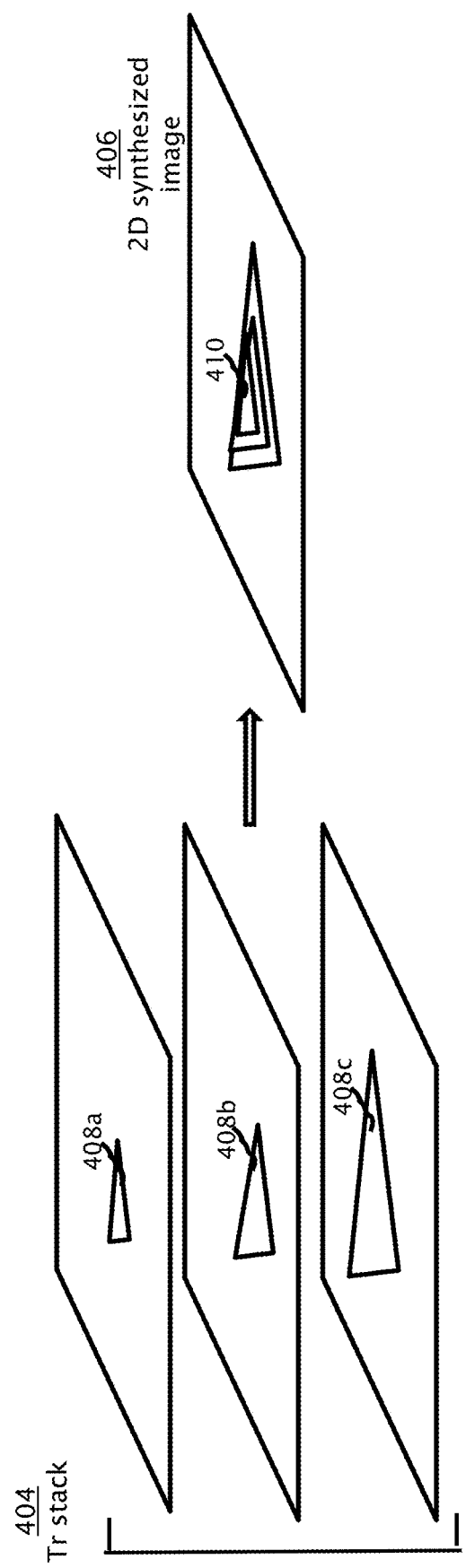
FIG. 4A-4D illustrate exemplary techniques for combining objects onto one or more 2D synthesized images.

FIG. 4A shows an example embodiment of an intra-object combination. Intra-object combination may refer to techniques used to represent a single object (that is captured on multiple Tr image slices 404) onto the 2D synthesized image. More particularly, an identified 3D object may appear in many consecutive Tr image slices as 408*a*, 408*b* and 408*c*. In theory these image patterns compete with each other for representation on the 2D synthesized image. Thus, an intra-object combination requires recognizing that all the images slices belong to the same 3D object, and only showing relevant information pertaining to the 3D object on the 2D synthesized image 406. Notably, as shown in FIG. 4A, the system may determine that all the image patterns 408*a*, 408*b* and 408*c* from the Tr stack 404 belong to the same 3D object, and may collapse them together such that they appear as one object 410 in the 2D synthesized image 406. In one or more embodiments, techniques such as averaging, MIP (maximum intensity projection), filtering, etc. may be used for intra-object combination. Intra-object combination techniques aim to preserve the structure of the 3D object without losing valuable information from any of the image slices, while minimizing competing information from multiple image slices that do not provide valuable information and/or visually confuse the end-user.

Figure 4B:
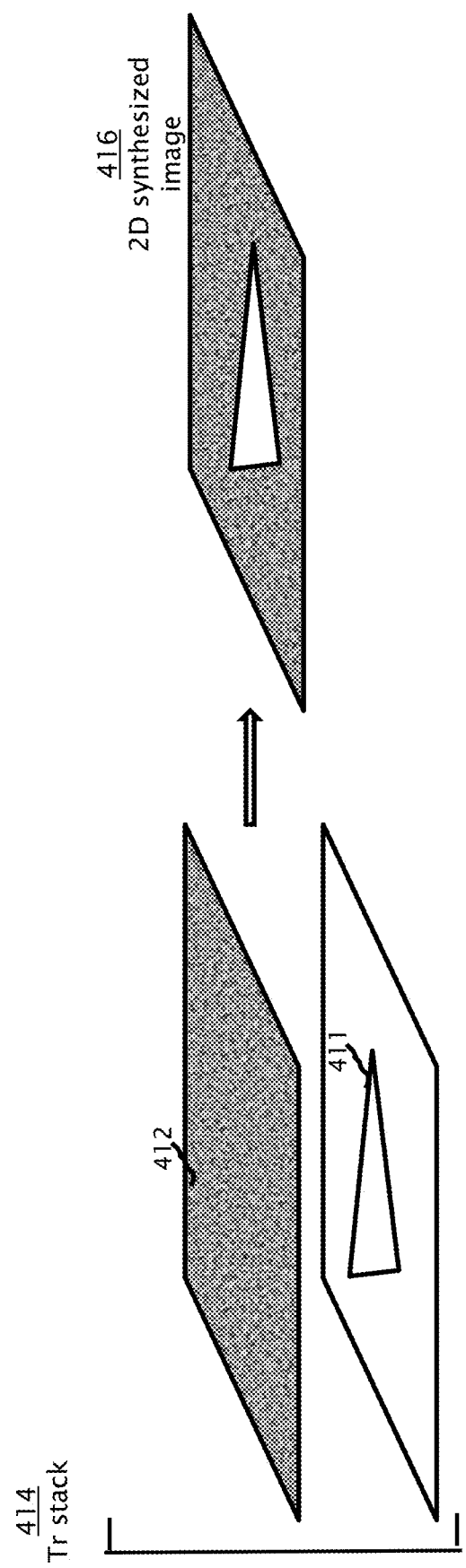

FIG. 4B illustrates an example embodiment of an object vs background combination. Object vs. background combination may be important for creating a natural-looking 2D synthesized image. The goal of this technique is to maintain useful information from objects together with meaningful background information representative of breast tissue. In the illustrated embodiment, the Tr stack 414 comprises two Tr image slices. The first image slice comprises a background image pattern 412. The second image slice comprises an object or a portion of an object 411. In collapsing information from the Tr stack 414 to the 2D synthesized image 416, some aspects of both image slices are emphasized while other aspects are de-emphasized. For example, in 2D synthesized image 416, the object 411 is preserved, and the background 412 is also rendered, but the middle portion of the background 412 is de-emphasized.

Figure 4C:
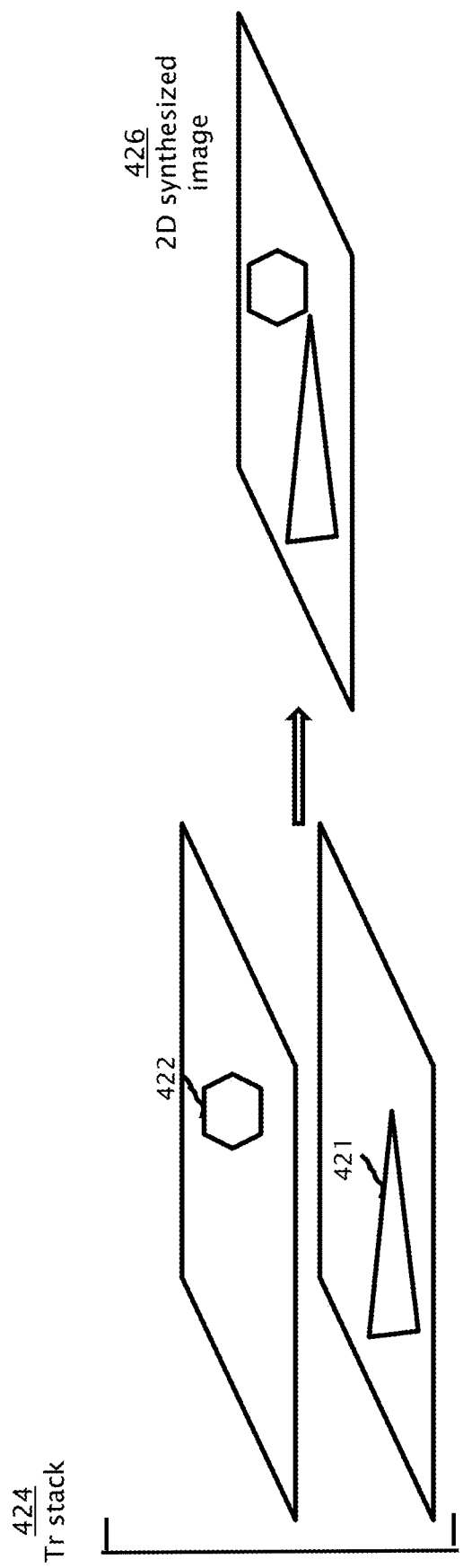

FIG. 4C illustrates an example embodiment of inter-object combination without overlapping. In the illustrated embodiment, Tr stack 424 comprises two Tr image slices. One Tr image slice comprises object 422, and the other Tr image slice comprises object 421. As shown in the illustrated embodiment, these objects do not overlap in the z direction. Thus, when collapsing both objects onto the 2D synthesized image 426, both objects 421 and 422 are represented clearly at their respective x-y locations.

Figure 4D:
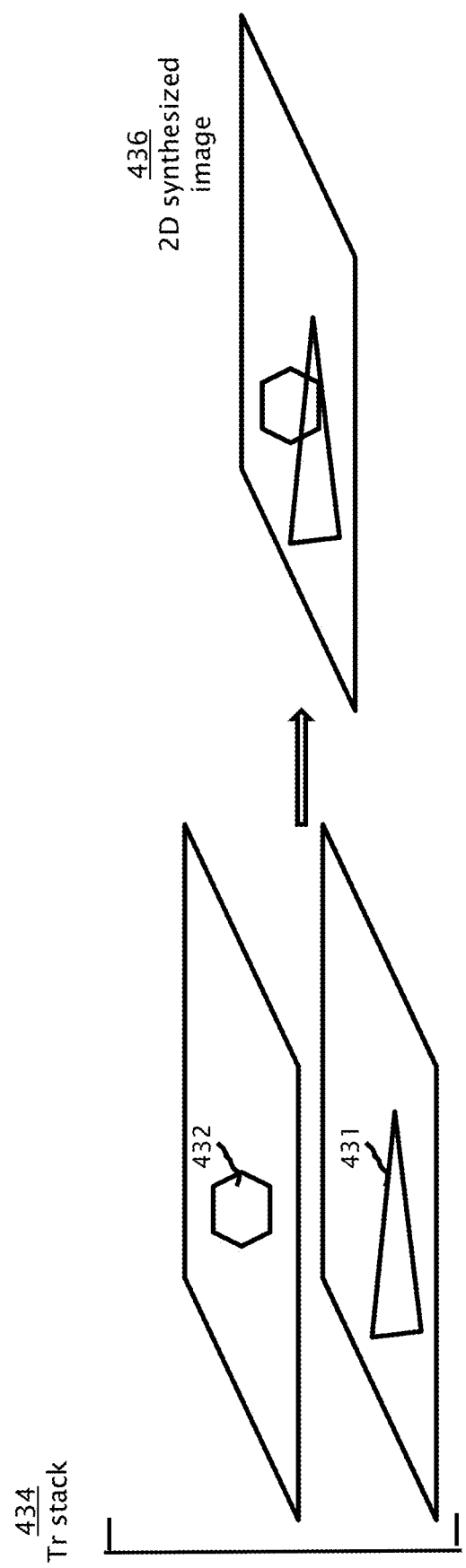

FIG. 4D illustrates an example embodiment of inter-object combination with overlap. This technique may be performed when two or more objects overlap to some degree. The two objects may be of the same type or of different types. In case of an overlap of objects, a hierarchical approach may be used to determine which object should be given precedence over the other. For example, if a higher weight is assigned to a first object, the first object may be emphasized in the 2D synthesized object, while the second object (or portions of the second object) may be de-emphasized. Or, if both objects are equally, or almost equally, important, both objects may be represented equally even if they are overlapping (and portions of both objects may be emphasized/de-emphasized such that both objects are clear in the synthesized 2D image).

In the illustrated embodiment, Tr image stack 434 comprises two Tr image slices. One Tr image slice comprises object 432, and the other Tr image slice comprises object 431. As shown in the illustrated embodiment, these objects overlap in the z direction. Thus, when collapsing the objects onto the 2D synthesized image 436, both objects 431 and 432 are represented, but are shown to overlap. Depending on weights assigned to both objects, one object may be highlighted while the other is de-emphasized. In the illustrated embodiment, both objects are represented somewhat equally, even though it is clear that they represent two separate objects. In other embodiments (not shown), if object 431 is assigned a higher weight/priority, object 431 may be emphasized in the foreground, while object 432 may be relegated to the background. Similarly, other combination techniques may be utilized to optimally represent clinically-significant information to the end-user.

Figure 5:
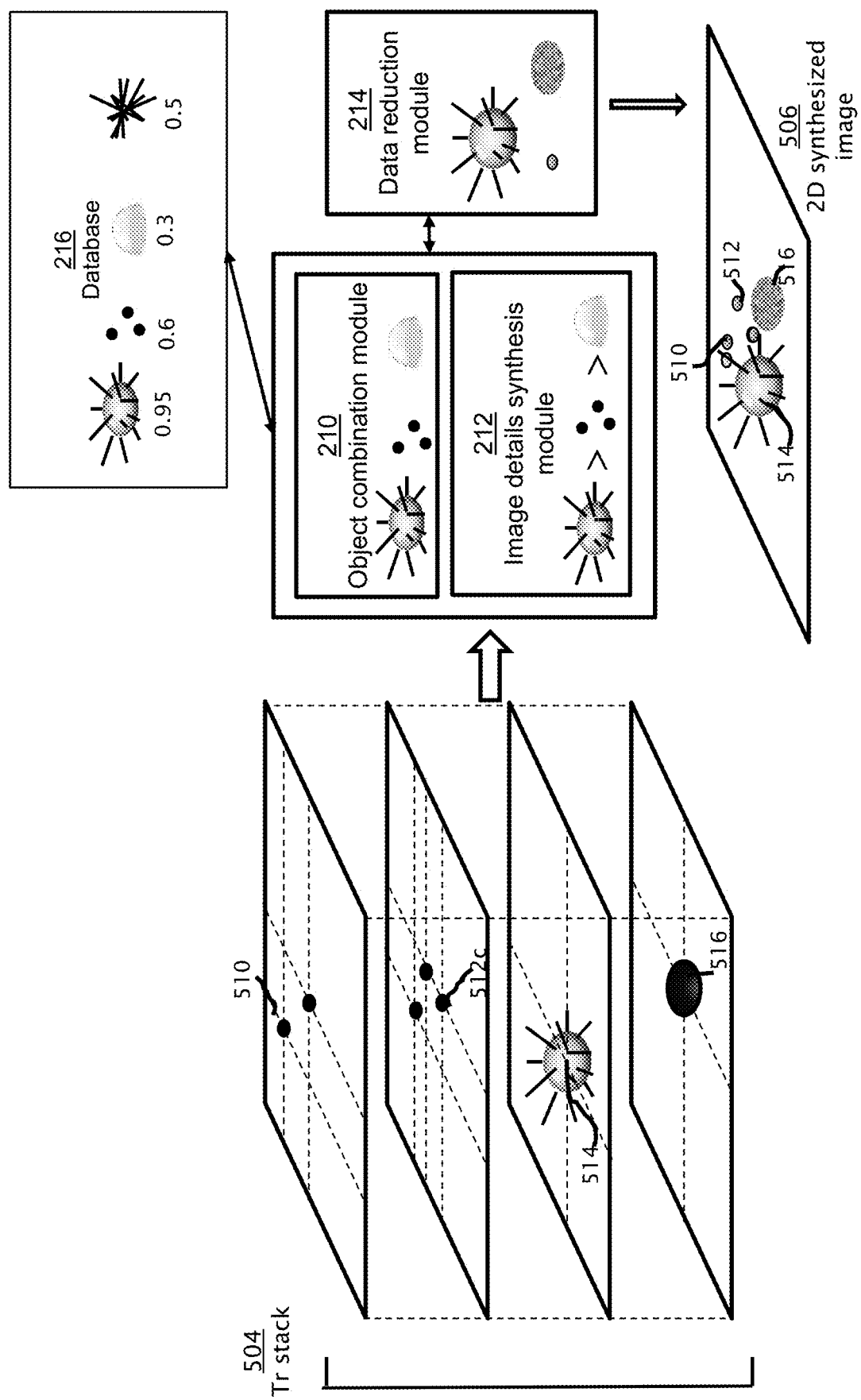
FIG. 5 illustrates an exemplary flow diagram depicting combining objects from a 3D object grid onto a 2D synthesized image.

FIG. 5 depicts an exemplary embodiment of collapsing information from a plurality of Tr images into a 2D synthesized image. In particular, a Tr image stack 504 may be used to create a 3D object grid similar to the 3D grid shown in FIG. 2. The Tr stack 504 illustrates four distinct objects including two calcification areas 510 and 512, a spiculated mass 514, and a spherical mass 516. As discussed in detail above, identifying these four objects as separate and distinct objects allows the system to accurately depict the objects as a whole on the 2D synthesized image 506. In the illustrated embodiment, the spiculated mass 514 is shown most prominently, while the calcifications and the spherical mass 516 are not as emphasized. This allows an end-user to easily identify the most clinically significant part of the 2D synthesized image without being overwhelmed with objects that are less-significant.

Figure 6:
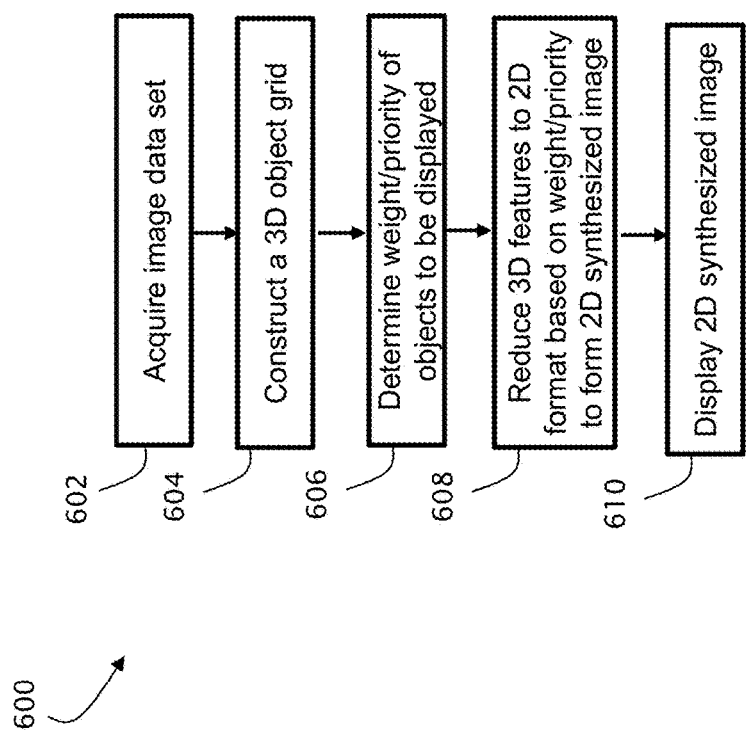
FIG. 6 illustrates an exemplary flow diagram depicting generating one or more 2D synthesized images using a 3D object grid.

FIG. 6 is a flow diagram 600 provided to illustrate exemplary steps that may be performed in an image merge process carried out in accordance with one embodiment of the disclosed inventions. At step 602, an image data set is acquired. The image data set may be acquired by a tomosynthesis acquisition system, a combination tomosynthesis/mammography system, or by retrieving pre-existing image data from a storage device, whether locally or remotely located relative to an image display device. At step 604, a 3D object grid may be constructed by identifying various objects that are present in a 3D coordinate space representative of a patient's breast tissue. At step 606, the objects of the 3D object grid are recognized, and a relative weight/priority of each of the objects is determined. As discussed above, in some embodiments, all objects of the 3D object grid may be displayed, with some objects emphasized more than others. In other embodiments, only a subset of the recognized objects may be displayed at all, while less-significant objects are omitted.

For example, it may be determined that one object is much more clinically significant as compared to another. Or, it may be determined that two overlapping objects are equally significant. In this case, algorithms aiming to visually depict both objects optimally may be utilized, rather than highlighting one object over another. At step 608, based on the relative weight/priority of the objects, the 3D objects may be reduced to a 2D format to create the 2D synthesized image. This reduction process may highlight one object over another, in some embodiments. In other embodiment, the reduction process may highlight an outline of an object while de-emphasizing an interior of the object.

In yet another embodiment, the reduction process may emphasize one or more features that are deemed to be significant, while de-emphasizing less significant aspects of the same object. For example, in the case of a spiculated lesion, it may be important to display the blood supply lines emanating from the center of the spiculated mass, but the center of the spiculated mass, even if dense may be displayed with less emphasis. Any number of such enhancement techniques may be used in the data reduction process. At step 610, the synthesized 2D image is displayed to the end-user.

Having described exemplary embodiments, it should be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments (e.g., the dimensions of various parts), without departing from the scope of the disclosed inventions, which is to be defined only by the following claims and their equivalents. The specification and drawings are, accordingly, to be regarded in an illustrative rather than restrictive sense.

What is claimed is:

1. A method for processing breast tissue image data, comprising:

processing an image data set including a plurality of image slices comprising image data of a patient's breast tissue to identify two or more clinically significant high-dimensional breast tissue objects in the breast tissue and to determine a clinically significant object type for each of the two or more clinically significant high-dimensional breast tissue objects;

generating a high-dimensional object grid depicting each of the two or more high-dimensional breast tissue objects in the patient's breast tissue found across one or more respective image slices of the image data set;

determining a confidence or probability of each of the two or more high-dimensional breast tissue objects depicted in the high-dimensional object grid;

generating a synthesized image comprising a lower-dimensional format version of each of the two or more high-dimensional breast tissue objects depicted in the high-dimensional object grid based at least in part upon the confidence or probability of each of the two or more high-dimensional breast tissue objects, wherein the confidence or probability is determined based at least in part on a weight assigned to each of the two or more high-dimensional breast tissue objects, and wherein the weights assigned to the two or more high-dimensional breast tissue objects is based on the respective object type, where generating the synthesized image comprises:

determining whether the two or more high-dimensional breast tissue objects are likely to overlap in the displayed synthesized image; and if it is determined that the two or more high-dimensional breast tissue objects are likely to overlap in the synthesized image, modifying at least one feature of at least one of the likely overlapping high-dimensional breast tissue objects such that one or more most clinically significant features of at least one of the likely overlapping high-dimensional breast tissue objects is displayed.

2. The method of claim 1, further comprising generating the image data set including the plurality of image slices that collectively depict the patient's breast tissue, wherein the high-dimensional object grid is generated based at least in part on the plurality of image slices.

3. The method of claim 1, wherein generating the synthesized image comprising the lower-dimensional format version of the two or more high-dimensional breast tissue objects includes modifying one or more aspects of at least one of the two or more high-dimensional breast tissue objects based at least in part on its respective determined confidence or probability.

4. The method of claim 1, wherein the lower-dimensional format version of the two or more high-dimensional breast tissue objects is based at least in part on an intra-object combination.

5. The method of claim 1, wherein the lower-dimensional format version of the two or more high-dimensional breast tissue objects is based at least in part on an inter-object combination.

6. The method of claim 1, wherein the lower-dimensional format version of the two or more high-dimensional breast tissue objects is based at least in part on combining a breast tissue object with a background.

7. The method of claim 1, further comprising displaying the synthesized image comprising the lower-dimensional format version of the two or more high-dimensional breast tissue objects.

8. The method of claim 1, wherein the high-dimensional object grid comprises two or more high-dimensional breast tissue objects that depict normal and/or abnormal breast tissue structures.

9. The method of claim 8, wherein the two or more high-dimensional breast tissue objects comprise a plurality of objects that collectively represent an entire breast parenchymal tissue structure.

10. The method of claim 8, wherein each of the two or more high-dimensional breast tissue objects is associated with a respective set of attributes, each attribute representing a characteristic of the breast tissue structure depicted by the respective high-dimensional breast tissue object.

11. The method of claim 10, wherein the set of attributes collectively represent one or more of a location, a size, a shape, and a morphology of the respective breast tissue structure depicted by the high-dimensional breast tissue object.

12. The method of claim 8, wherein the two or more high-dimensional breast tissue objects include two or more high-dimensional breast tissue objects corresponding to a first object type, and two or more high-dimensional breast tissue objects corresponding to a second object type.

13. The method of claim 12, wherein the first object type corresponds to abnormal breast lesions including microcalcifications and masses, and the second object type corresponds to normal breast structures including nipples, pectoral muscles, and breast parenchymal tissues.

14. The method of claim 13, wherein a weight assigned to objects of the first object type is greater than a weight assigned to objects of the second object type.

15. The method of claim 12, further comprising using a pattern recognition method for each of the first and second object types to determine whether one or both object types are present in the image data set that depicts the patient's breast tissue.

16. The method of claim 15, wherein the pattern recognition method utilizes one or more machine learning algorithms.

17. The method of claim 1, further comprising, if it is determined that displaying both the two or more high-dimensional breast tissue objects that are likely to overlap in the synthesized image.

18. The method of claim 1, wherein modifying at least one feature of at least one of the overlapping high-dimensional breast tissue objects comprises modifying the object to emphasizing a first portion of the modified high-dimensional breast tissue object relative to a second portion of the same object.

19. A method for processing breast tissue image data, comprising:
  processing an image data set including a plurality of image slices comprising image data of a patient's breast tissue to identify two or more clinically significant high-dimensional breast tissue objects in the breast tissue and to determine a clinically significant object type for each of the two or more clinically significant high-dimensional breast tissue objects;
  generating a high-dimensional object grid depicting each of the two or more high-dimensional breast tissue objects in the patient's breast tissue found across one or more respective image slices of the image data set;
  determining a confidence or probability of each of the two or more high-dimensional breast tissue objects depicted in the high-dimensional object grid;
  generating a synthesized image comprising a lower-dimensional format version of each of the two or more high-dimensional breast tissue objects depicted in the high-dimensional object grid based at least in part upon the confidence or probability of each of the two or more high-dimensional breast tissue objects, wherein the confidence or probability is determined based at least in part on a weight assigned to each of the two or more high-dimensional breast tissue objects, and wherein the weights assigned to the two or more high-dimensional breast tissue objects is based on the respective object type,
  where generating the synthesized image comprises:
    determining whether two of the two or more high-dimensional breast tissue objects are likely to overlap in the displayed synthesized image; and
    if it is determined that the two of the two or more high-dimensional breast tissue objects are likely to overlap in the synthesized image:
      determining a difference in assigned weight of each of the two of the two or more high-dimensional breast tissue objects likely to overlap, and
      if the determined difference is lower than a threshold value,
        modifying one or more aspects of at least one of two of the two or more high-dimensional breast tissue objects, and
        displaying both of the two of the two or more high-dimensional breast tissue objects likely to overlap in the synthesized image, wherein the modification pertains to emphasizing at least a portion of the high-dimensional breast tissue object assigned the higher weight relative to the high-dimensional object assigned the lower weight.

20. The method of claim 19, wherein generating the synthesized image comprising the lower-dimensional format version of the respective two or more high-dimensional breast tissue objects includes modifying one or more aspects of at least one of the two or more high-dimensional breast tissue objects to thereby emphasize high-dimensional breast tissue objects corresponding to the first object type over high-dimensional breast tissue objects corresponding to the second object type.

21. The method of claim 19, further comprising, if the determined difference is equal to or greater than the threshold value, displaying only one of the two of the two or more high-dimensional breast tissue objects likely to overlap in the synthesized image, the displayed object being the one assigned the higher weight.

22. The method of claim 19, wherein the first portion comprises an outline portion of the modified high-dimensional breast tissue object, and the second portion comprises a middle portion of the same object.

23. The method of claim 19, further comprising, if the determined difference is lower than a threshold value, modifying at least one of the two of the two or more high-dimensional breast tissue objects to emphasizing a first portion of the modified high-dimensional breast tissue object relative to a second portion of the same object.

* * * * *